(12) United States Patent
Mertoglu et al.

(10) Patent No.: US 10,196,482 B2
(45) Date of Patent: Feb. 5, 2019

(54) MIXED ALKYL TERMINATED POLYETHER DENDRONS

(71) Applicant: BASF SE, Ludwigshafen (DE)

(72) Inventors: Murat Mertoglu, Ludwigshafen (DE); Jean-Pierre Berkan Lindner, Mannheim (DE); Ann-Kathrin Marguerre, Mannheim (DE); Rainer Berghaus, Speyer (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/307,586

(22) PCT Filed: Apr. 20, 2015

(86) PCT No.: PCT/EP2015/058464
§ 371 (c)(1),
(2) Date: Oct. 28, 2016

(87) PCT Pub. No.: WO2015/165760
PCT Pub. Date: Nov. 5, 2015

(65) Prior Publication Data
US 2017/0051107 A1    Feb. 23, 2017

(30) Foreign Application Priority Data

Apr. 30, 2014   (EP) .................................... 14166568

(51) Int. Cl.
| | | |
|---|---|---|
| C08G 65/26 | (2006.01) |
| A01N 31/02 | (2006.01) |
| C08G 65/24 | (2006.01) |
| C08L 71/02 | (2006.01) |
| C08G 83/00 | (2006.01) |
| A01N 25/30 | (2006.01) |
| C08G 65/331 | (2006.01) |

(52) U.S. Cl.
CPC ......... *C08G 65/2609* (2013.01); *A01N 25/30* (2013.01); *A01N 31/02* (2013.01); *C08G 65/24* (2013.01); *C08G 65/331* (2013.01); *C08G 83/003* (2013.01); *C08L 71/02* (2013.01); *C08G 2650/24* (2013.01); *C08G 2650/32* (2013.01)

(58) Field of Classification Search
USPC ....................................................... 504/362
See application file for complete search history.

(56) References Cited

U.S. PATENT DOCUMENTS

| | | |
|---|---|---|
| 8,492,497 B2 | 7/2013 | Al-Hellani et al. |
| 8,841,382 B2 | 9/2014 | Cristadoro et al. |
| 2011/0015361 A1 | 1/2011 | Al-Hellani et al. |
| 2012/0053057 A1 | 3/2012 | Cristadoro et al. |
| 2012/0082629 A1* | 4/2012 | Turk ........................ A61K 8/87 424/54 |

FOREIGN PATENT DOCUMENTS

| | | |
|---|---|---|
| EP | 2 100 621 | 9/2009 |
| WO | WO-2010/000713 | 1/2010 |
| WO | WO-2011/006838 | 1/2011 |
| WO | WO-2012/029038 | 3/2012 |
| WO | WO-2016/041693 | 3/2016 |

OTHER PUBLICATIONS

Grayson et al., "Synthesis and Surface Functionalization of Aliphatic Polyether Dendrons," *Journal of the American Chemical Society*, 2000, vol. 122, No. 42, pp. 10335-10344.
Jayaraman et al., "A Convergent Route to Novel Aliphatic Polyether Dendrimers," *Journal of the American Chemical Society*, 1998, vol. 120, No. 49, pp. 12996-12997.

(Continued)

*Primary Examiner* — Sreenivasan Padmanabhan
*Assistant Examiner* — Courtney A Brown
(74) *Attorney, Agent, or Firm* — Brinks Gilson & Lione

(57) ABSTRACT

A polyether dendrimer of formula (I), $$Y_n \sim \left[ \!\!\!\begin{array}{c} \\ \end{array}\!\!\! \right\rangle\!\!\!-\!\!\!\left[ O \right]_m\!\!\!-\!\!X$$
$$Z_o \sim$$

wherein the symbols and indices have the following meanings:
each Y is independently $[R^1-(O-CH_2-CH_2)_p-O-]$;
each Z is independently $[R^2-(O-CH_2-CH_2)_q(O-CH(CH_3)-CH_2)_r-O-]$;
each $R^1$ is independently H, $CH_3$ or $C_2$-$C_4$-alkyl;
each $R^2$ is independently linear or branched $C_8$-$C_{22}$-alkyl;
X is H or $C_1$-$C_4$-alkyl;
m is 1, 2, 3, 4, 5 or 6;
n, o are rational positive numbers >0, with the proviso that the sum of n and o is $2^m$;
p is a natural number from 5 to 50;
q is a natural number from 1 to 50;
r is 0 or is a natural number from 1 to 30, with the proviso that $5 \leq q+r \leq 50$, and
~ denotes the bonding of the respective group to the dendron scaffold,
is useful for solubilizing sparingly-water soluble active ingredients, in particular pesticides.

16 Claims, No Drawings

(56) References Cited

OTHER PUBLICATIONS

Richter et al., "Non-Ionic Dendriticglycerol-Based Amphiphiles: Novel Excipients for the Solubilization of Poorly Water-Soluble Anticancer Drug Sagopilone," *European Journal of Pharmaceutical Sciences*, 2010, vol. 40, pp. 48-55.
Search Report dated Jul. 3, 2014 for European Application No. 14166568.7.
International Search Report dated May 8, 2015 for PCT/EP2015/058464.
International Preliminary Report on Patentability dated Jul. 21, 2016 for PCT/EP2015/058464.

* cited by examiner

MIXED ALKYL TERMINATED POLYETHER DENDRONS

This application is a National Stage application of International Application No. PCT/EP2015/058464, filed Apr. 20, 2015. This application also claims priority under 35 U.S.C. § 119 to European Patent Application No. 14166568.7, filed Apr. 30, 2014.

The invention relates to polyether dendrons, a process for their preparation and their use for solubilizing sparingly water soluble active ingredients. It further relates to a composition comprising a polyether dendron and a sparingly water-soluble active ingredient, a process for its preparation and uses of the composition, in particular for controlling phytopathogenic fungi and/or unwanted vegetation and/or unwanted insect or acarid infestation and/or for regulating the growth of plants.

In many cases, it is necessary to solubilize hydrophobic active ingredients in water without chemically altering the active ingredient in question as such. For this purpose, it is possible, for example, to prepare an emulsion, in which case the active ingredient in question is present in the oil phase of the emulsion. However for many active pharmaceutical ingredients, or in particular crop protection compositions, especially for those which are to be transported with a body fluid or in a plant's sap, an approach of this kind is not possible. Emulsions can break under the action of high shear forces. Moreover, sterilization, for example for active pharmaceutical ingredients, while maintaining the emulsion is not possible in many cases.

Hyperbranched polyethers and processes for their preparation and modification are known in the art:

WO 2010/000713 discloses linear dendritic polyglycerol compounds and preparation thereof by means of a "CLICK reaction" (1,3-dipolar cycloaddition of alkyne and azide to form a triazole ring). These compounds can be used to solubilize hydrophobic substances.

EP 2 100 621 discloses linear dendritic polyglycerol compounds and preparation thereof by means of a "CLICK reaction".

Grayson and Frechet (J. Am. Chem. Soc. 2000, 122, 10335-10344) disclose the synthesis and functionalization of aliphatic polyether dendrons.

Jayaraman and Frechet (J. Am. Chem. Soc. 1998, 120, 12996-12997) disclose the synthesis of aliphatic polyether dendrons and the silylation of the focal hydroxyl group.

Richter et al. (Europ. J. Pharm. Sci. 2010, 40 (1), 48-55) disclose the preparation of nonionic dendritic glycerol-based amphiphiles by means of a "CLICK reaction".

WO 2012/029038 discloses hyperbranched polyethers comprising polyethyleneglycol monomethylether groups.

A disadvantage of the known hyperbranched polyethers and the preparation processes therefor is that they require very costly reactants, especially for the CLICK reaction. It was therefore not possible to employ the known preparation processes industrially. A further disadvantage was that the known compounds can solubilize only small amounts of sparingly soluble active ingredients, since they do not usually possess a markedly amphiphilic structure. A further disadvantage is that the polarity of the amphiphiles can be adjusted only very roughly, for example by exchanging one anionic end group for another kind of anionic end group.

It was an object of the present invention to overcome the aforementioned disadvantages. In addition, the intention was to find compounds obtainable by a simple preparation process based on industrially available reactants. The amphiphilic thus prepared was to make available high concentrations of sparingly soluble active ingredients, such as pesticides, in aqueous solutions.

The object is achieved by a polyether dendron of formula (I), $$Y_n \sim \rangle\!\!-\!\!O\!\!-\!\!X \\ Z_o \sim \quad\quad\quad ]_m \quad\quad (I)$$

wherein the symbols and indices have the following meanings:

each Y is independently $[R^1-(O-CH_2-CH_2)_p-O-]$;
each Z is independently $[R^2-(O-CH_2-CH_2)_q(O-CH(CH_3)-CH_2)_r-O-]$;
each $R^1$ is independently H, $CH_3$ or $C_2$-$C_4$-alkyl;
each $R^2$ is independently linear or branched $C_8$-$C_{22}$-alkyl;
X is H or C, $C_1$-$C_4$-alkyl;
m is 1, 2, 3, 4, 5 or 6;
n, o are rational positive numbers>0, with the proviso that the sum of n and o is $2^m$;
p is a natural number from 5 to 50;
q is a natural number from 1 to 50;
r is 0 or is a natural number from 1 to 30, with the proviso that $5 \leq q+r \leq 50$, and
~ denotes the bonding of the respective group to the dendron scaffold.

In a further aspect of the invention there is provided a process for preparing a polyether dendron of the invention, comprising the steps of reacting n moles (Y—H) and o moles (Z—H) with (n+o)/2 moles of glycerol or a reactive derivative thereof, like epichlorohydrin, at a temperature of 20 to 200° C. and optionally in the presence of a catalyst, like an inorganic or organic base, and optionally repeating the step of reacting with glycerol or a reactive derivative thereof up to the number of m reactions, reacting each time half of the molar amount of glycerol or reactive glycerol derivative reacted in the last step.

In yet a further aspect of the invention there is provided the use of a polyether dendron of the invention in a composition comprising an active ingredient, in particular in a pesticidal or pharmaceutical composition.

In another aspect of the invention there is provided the use of a polyether dendron of the invention for increasing the water-solubility of sparingly water-soluble active ingredients in aqueous solutions.

In yet a further aspect of the invention there is provided a composition, comprising
a) a polyether dendron of the invention and
b) an active ingredient, in particular a pesticidal or pharmaceutical active ingredient.

In yet a further aspect of the invention there is provided a process for producing the composition of the invention comprising the step of contacting a polyether dendron of the invention and a pesticidal or pharmaceutical active ingredient.

In yet a further aspect of the invention there is provided a method for controlling phytopathogenic fungi or undesired vegetation or insect or acarid infestations or for regulating the growth of plants, comprising the step of applying a composition of the invention to the pests or undesired plants, to plants to be protected and/or to the soil where the plants to be protected or the undesired plants grow.

Advantages of the invention are that a high concentration of active ingredient can be brought into solution; that the preparation of the polyether dendron is possible in a very simple manner and on an industrial scale; and that the polyether dendron itself is water-soluble or water-dispersible. In addition, it is possible to provide polyether dendrons without anionic groups, such that there cannot be any unwanted interaction with the active ingredients or other formulation excipients in compositions comprising active ingredient. It is also possible to very finely adjust the polarity of the dendron, e.g. through the ratio and nature of $R^1$ and $R^2$ or via the length of the polyalkylene oxide chains in Y and Z. In addition, the compositions of the invention show an improved storage stability.

Throughout the application, combinations of preferred features with other preferred features are encompassed by the invention.

"Polyether dendron of the invention" as used herein means the polyether dendrons of formula (I) and their preferred embodiments.

In the formula (I) the symbols and indices preferably have the following meanings:

X is preferably H.

Each Y is preferably the same, and is the group mentioned above.

Each Z is preferably the group mentioned above.

$R^1$ is preferably $CH_3$.

$R^2$ is preferably linear, preferably linear $C_8$-$C_{22}$-alkyl.

m is preferably 2 or 3.

n, o are preferably positive rational numbers with the proviso that the sum of n and o is $2^m$.

p is preferably a natural number from 15 to 25.

q is preferably a natural number from 5 to 25.

r is preferably 0 or is a natural number from 1 to 15.

Preferred are polyether dendrons of formula (I) where all symbols and indices have the preferred meanings.

In more preferred embodiments of the invention the symbols and indices in formula (I) have the following meanings X is more preferably H.

Y is more preferably the same, and is the group mentioned above.

Z is more preferably the group mentioned above.

$R^1$ is more preferably $CH_3$.

$R^2$ is more preferably linear $C_8$-$C_{22}$-alkyl.

m is more preferably 2 or 3.

n, o are more preferred rational positive numbers, with the provisos that $0.25 \leq o \leq 4$ n and $n+o=2^m$.

p is more preferred 15 to 25.

q is more preferred 15 to 25.

r is more preferred 0 or is 1 to 5.

More preferred are polyether dendrons of the formula (I), where all the symbols and indices have the more preferred meanings.

The polyether dendrons of formula (I) generally have a molecular weight of 1060 to 15.000, preferably 3000 to 6000, as determined by GPC with a poly methylmethacrylate (PMMA) standard. Preferably the column material is a polyester copolymer. Dimethylacetamide is preferably used as a solvent.

The group Y generally has a molecular weight of 300 to 2000, preferably 750 to 1000, as determined by GPC.

Suitable methyl polyethylene glykols (MPEGs) are known and are commercially available, e.g., as Pluriol® A 350 E and Pluriol® A 1020 from BASF SE or Carbowax® 350 and 750 from Dow Chemicals.

The group Z generally has a molecular weight of from 300 to 2000. Suitable alkyl polyalkylene glykols (FAPEGs) are known and commercially available, e.g., as Lutensol® AT 11 from BASF SE or Genapol® T200-800 and Genapol® LA070, 160 from Clariant.

As the fatty alcohols $R^2$—OH often derive from natural sources it is common to have mixtures, e.g. of $C_{16}$ and $C_{18}$ alcohols or $C_{12}$ and $C_{14}$ alcohols.

The weight ratio Y:Z is generally in the range of from 13:1 to 1:3, preferably 7:1 to 1:1, more preferred 4:1 to 2:1.

The molar ratio of Y to Z is generally in the range of from 95:5 to 3:7 preferably 15:1 to 1:1, more preferred 2.5:1 to 1:1.

In general 70 to 100% of the groups Y and Z carry an end group $R^1$ or $R^2$, preferably at least 95%.

The polyether dendron of the formula (I) comprises a group of the formula (II):

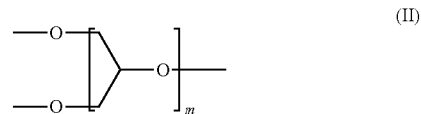

Such a group typically has only perfectly branched units with no defects.

In a preferred embodiment the polyether dendron of formula (I) is a mixture of different dendrons of different generations, expressed by different parameters m.

Typical examples of the polyether dendrons of formula (I) are shown in the following, where W is a group $[R^1—(O—CH_2—CH_2)_p]$ or $[R^2—(O—CH_2—CH_2)_q(O—CH(CH_3)—CH_2)_r]$:

m = 1:

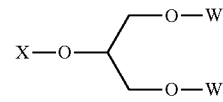

m = 2:

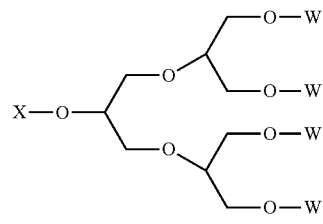

m = 3:

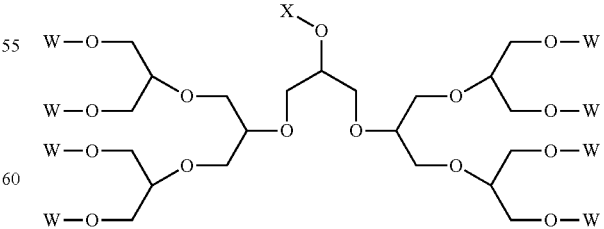

In one embodiment of the invention, the polyether dendrons of the formula (I) are contaminated with products of an incomplete reaction. Owing to an incomplete reaction, the following compounds, for example, may then be formed:

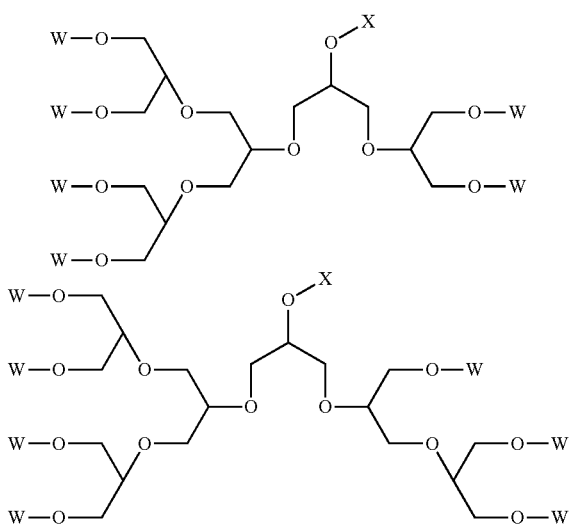

The polyether dendrons of formula (I) are preferably prepared by linking in the monomers so as to form structures from the periphery until monofunctional, tree-like structures are finally obtained (convergent approach). In this context, "monofunctional" is understood to mean the monofunctionality of the focal unit.

A further approach consists in proceeding from a central molecule, by controlled stepwise linkage of in each case two or more di- or polyfunctional monomers to each monomer already bound (divergent approach). With each linkage step, this multiplies the number of monomer end groups (and hence of linkages) by a factor of 2 or higher, giving monodisperse polymers built up generation by generation and having tree-like structures, the branches of which each comprise exactly the same number of monomer units.

The polyether dendrons of formula (I) can be prepared by methods generally known in the art, for example from WO 2011/006838. The advantage of such dendrons is that they are preparable in a simple manner without use of protecting groups. Well-defined monofunctional macromolecules are thus obtained via a convergent approach in a multistage process. Optionally, if there is a desire to dispense with separating processes for economic reasons, mixtures of different monofunctional macromolecules are obtained. The mixtures then consist of a plurality of dendrons of different generations (different parameters m).

To prepare the dendrons of formula (I), compounds of the general formulae W—OH are reacted with glycerol or preferably a reactive derivative of glycerol (such as epichlorohydrin, glycidol or glyceryl carbonate), especially with epichlorohydrin. For this purpose, it is preferable to select a molar ratio of the compounds general formulae W—OH to reactive derivative of glycerol, especially epichlorohydrin, such as 2:1. The preparation can be performed for example, at temperatures in the range from 20 to 200° C., preferably at 80 to 130° C. The preparation can be performed in the presence of a catalyst. Suitable catalysts are, for example inorganic and organic bases. If epichlorohydrin is used as the reactive glycerol derivative, the base not only serves as a catalyst but also to neutralize the hydrochloric acid formed. Suitable inorganic bases are, for example, alkali metal carbonates and especially alkali metal hydroxides, such as NaOH and KOH. Suitable organic bases are, for example, tertiary amines, especially triethylamine and [2.2.2]diazabicyclooctane (DABCO), and also pyridine and para-N,N-dimethylaminopyridine. In one embodiment, the preparation can be performed in a solvent. Suitable solvents are, for example, ethers, especially 1,4-dioxane, diisopropyl ether, tetrahydrofuran ("THF") and di-n-butyl ether. Further suitable solvents are n-butyl acetate ("butyl acetate"), DMSO, N,N-dimethylformamide ("DMF") and N-methylpyrrolidone, and aromatic solvents, for example toluene.

In embodiments in which water is eliminated in the preparation, it is possible to use desiccating agents, for example molecular sieve, sodium sulfate, magnesium sulfate, or the water formed can be removed by azeotropic distillation. In one embodiment of the invention, the reaction is performed over a period of 15 minutes to 48 hours, preferably 1 to 24 hours, more preferably 3 to 15 hours.

In one embodiment of the invention, the reaction is performed in stages, and in as many stages as correspond to the desired m. This involves adding reactive derivative of glycerol, especially epichlorohydrin, in the number of stages in question. For the stage by stage reaction, the procedure may be, for example, first to react a particular amount of compounds of the general formulae Y—OH and Z—OH with half the number of moles of glycerol or preferably with a reactive derivative of glycerol, especially with epichlorohydrin. Thereafter, an amount of glycerol or of reactive derivative of glycerol which corresponds to a quarter of the number of moles of compounds of the general formula W—OH are added, and reacted. If it is desired to perform a further stage an amount of glycerol or of reactive derivative of glycerol which corresponds to an eighth of the number of moles of compounds of the general formula W—OH is added thereafter, and reacted. In each further stage, the number of moles of compounds of the general formulae W—OH added is reduced correspondingly.

The focal hydroxyl group is understood to mean the single terminal OH group in the hyperbranched polyether of the formula (I).

One embodiment of the inventive preparation comprises the reaction of the focal hydroxyl group of the polyether dendron of the formula (I) with an OH-reactive group to prepare dendrons where X is $C_1$-$C_4$-alkyl.

The invention further relates to a composition comprising a polyether dendron of the formula (I) and an active ingredient, preferably a sparingly water-soluble active ingredient, in particular a pesticidal or pharmaceutical active ingredient.

"Active ingredient" as used herein means a physiologically active substance from the field of pesticides, pharmaceuticals, nutrition and cosmetics.

The composition comprises one or more different active ingredients. Examples of active ingredients are active pesticidal ingredients, active cosmetic ingredients, active pharmaceutical ingredients or food supplements (such as vitamins or carotenoids). Preferred active ingredients are pesticidal active ingredients and pharmaceutical active ingredients, in particular pesticidal active ingredients.

The active ingredient is preferably sparingly water soluble.

According to the invention, the maximum solubility of a sparingly-water soluble active ingredient in water at 20° C. is 10 g/l, preferably 2 g/l, more preferably 0.5 g/l and especially 0.1 g/l.

Examples of pesticidal active ingredients are listed below.

Examples of active pharmaceutical ingredients include: benzodiazepines, antihypertensives, vitamins, cytostatics, especially taxol, anesthetics, neuroleptics, antidepressives, antiviral agents, for example anti-HIV agents, antibiotics, antimycotics, antidementia drugs, fungicides, chemotherapeutics, urologics, platelet aggregation inhibitors, sulfonamides, spasmolytics, hormones, immunoglobulins, sera, thyroid therapeutics, psychoactive drugs, Parkinson's drugs and other antihyperkinetics, ophthalmics, neuropathy preparations, calcium metabolism regulators, muscle relaxants, anesthetics, lipid-lowering drugs, hepatotherapeutics, coronary drugs, cardiac drugs, immunotherapeutics, regulatory peptides and inhibitors thereof, hypnotics, sedatives, gynecologicals, gout remedies, fibrinolytics, enzyme preparations and transport proteins, enzyme inhibitors, emetics, blood flow stimulators, diuretics, diagnostic agents, corticoids, cholinergics, biliary therapeutics, antiasthmatics, bronchodilators, beta receptor blockers, calcium antagonists, ACE inhibitors, arteriosclerosis drugs, antiinflammatories, anticoagulants, antihypotensives, antihypoglycemics, antihypertensives, antifibrinolytics, antiepileptics, antiemetics, antidotes, antidiabetics, antiarrhythmics, antianemics, antiallergics, anthelmintics, analgesics, analeptics, aldosterone antagonists, slimming agents.

Examples of active cosmetic ingredients are cosmetic oils, flavorings and aromas, vitamins or UV absorbers. Cosmetic oils include peanut oil, jojoba oil, coconut oil, almond oil, olive oil, palm oil, castor oil, soybean oil, wheatgerm oil, or essential oils such as mountain pine oil, lavender oil, rosemary oil, spruce needle oil, pine needle oil, eucalyptus oil, peppermint oil, sage oil, bergamot oil, turpentine oil, melissa oil, juniper oil, lemon oil, anise oil, cardamom oil, camphor oil, etc., or mixtures thereof. UV absorbers include 2-hydroxy-4-methoxybenzophenone, 2,2',4,4'-tetrahydroxybenzophenone, 2,2'-dihydroxy-4,4'-dimethoxybenzophenone, 2,4-dihydroxybenzophenone, 2'-ethylhexyl 2-cyano-3,3-diphenylacrylate, 2,4,6-trianilino-p-(carbo-2'-ethylhexyl-1'-oxy)-1,3,5-triazine, 3-(4-methoxybenzylidene)camphor, 2-ethylhexyl N,N-dimethyl-4-aminobenzoate, 3,3,5-trimethylcyclohexyl salicylate, 4-isopropyldibenzoylmethane, 2-ethylhexyl p-methoxycinnamate and 2-isoamyl p-methoxycinnamate, and mixtures thereof.

Examples of flavorings and aromas are as described, e.g., in WO 01/49817, or in "Flavors and Fragrances", Ullmann's Encyclopedia of Industrial Chemistry, Wiley-VCH, 2002, to which explicit reference is made.

Examples of vitamins are vitamins, provitamins and vitamin precursors from groups A, C, E and F, especially 3,4-didehydroretinol, beta-carotene (provitamin of vitamin A), ascorbic acid (vitamin C), and the palmitic esters, glucosides or phosphates of ascorbic acid, tocopherols, especially alpha-tocopherol and esters thereof, for example the acetate, the nicotinate, the phosphate and the succinate; and additionally vitamin F, which is understood to mean essential fatty acids, particularly linolic acid, linolenic acid and arachidonic acid.

The active ingredient is more preferably a pesticidal active ingredient, preferably a sparingly-water soluble pesticidal active ingredient.

The term "pesticidal active ingredients" (also referred to hereinafter as pesticides) refers to at least one active ingredient selected from the group of fungicides, insecticides, nematicides, herbicides, safeners and/or growth regulators. The term "insecticide" as used herein encompasses compounds with insecticidal and/or accaricidal activity. Preferred pesticides are fungicides, insecticides and herbicides, especially fungicides. Mixtures of pesticides from two or more of the abovementioned classes can also be used. The person skilled in the art is familiar with such pesticides, which can be found, for example, in The Pesticide Manual, 16$^{th}$ Ed. (2012), The British Crop Protection Council, London. Suitable fungicides are, e.g., fungicides of the classes dinitroanilines, allylamines, anilinopyrimidines, antibiotics, aromatic hydrocarbons, benzenesulfonamides, benzimidazoles, benzisothiazoles, benzophenones, benzothiadiazoles, benzotriazines, benzylcarbamates, carbamates, carboxamides, carboxylic acid amides, chloronitriles, cyanoacetamide oximes, cyanoimidazoles, cyclopropanecarboxamides, dicarboximides, dihydrodioxazines, dinitrophenylcrotonates, dithiocarbamates, dithiolanes, ethylphosphonates, ethylaminothiazolecarboxamides, guanidines, hydroxy-(2-amino)pyrimidines, hydroxyanilides, imidazoles, imidazolinones, inorganic compounds, isobenzofuranones, methoxyacrylates, methoxycarbamates, morpholines, N-phenylcarbamates, oxazolidinediones, oximinoacetates, oximinoacetamides, peptidylpyrimidine nucleosides, phenylacetamides, phenylamides, phenylpyrroles, phenylureas, phosphonates, phosphorothiolates, phthalamic acids, phthalimides, piperazines, piperidines, propionamides, pyridazinones, pyridines, pyridinylmethylbenzamides, pyrimidinamines, pyrimidines, pyrimidinonehydrazones, pyrroloquinolinones, quinazolinones, quinolines, quinones, sulfamides, sulfamoyltriazoles, thiazolecarboxamides, thiocarbamates, thiophanates, thiophenecarboxamides, toluamides, triphenyltin compounds, triazines, triazoles. Suitable insecticides are, e.g., insecticides from the class of carbamates, organophosphates, organochlorine insecticides, phenylpyrazoles, pyrethroids, neonicotinoids, spinosins, avermectins, milbemycins, juvenile hormone analogs, alkyl halides, organotin compounds, nereistoxin analogs, benzoylureas, diacylhydrazines, METI acaricides, and insecticides such as chloropicrin, pymetrozine, flonicamid, clofentezine, hexythiazox, etoxazole, diafenthiuron, propargite, tetradifon, chlorfenapyr, DNOC, buprofezin, cyromazine, amitraz, hydramethylnon, acequinocyl, fluacrypyrim, rotenone, or derivatives thereof.

Suitable herbicides are, e.g., herbicides of the classes of acetamides, amides, aryloxyphenoxypropionates, benzamides, benzofuran, benzoic acids, benzothiadiazinones, bipyridylium, carbamates, chloroacetamides, chlorocarboxylic acids, cyclohexanediones, dinitroanilines, dinitrophenol, diphenyl ethers, glycines, imidazolinones, isoxazoles, isoxazolidinones, nitriles, Nphenylphthalimides, oxadiazoles, oxazolidinediones, oxyacetamides, phenoxycarboxylic acids, phenylcarbamates, phenylpyrazoles, phenylpyrazolines, phenylpyridazines, phosphinic acids, phosphoroamidates, phosphorodithioates, phthalamates, pyrazoles, pyridazinones, pyridines, pyridinecarboxylic acids, pyridinecarboxamides, pyrimidinediones, pyrimidinyl(thio)benzoates, quinolinecarboxylic acids, semicarbazones, sulfonylaminocarbonyltriazolinones, sulfonylureas, tetrazolinones, thiadiazoles, thiocarbamates, triazines, triazinones, triazoles, triazolinones, triazolocarboxamides, triazolopyrimidines, triketones, uracils, ureas.

In one embodiment, the pesticide comprises a fungicide; the pesticide preferably consists of at least one fungicide. Examples of fungicides are fluxapyroxad, pyraclostrobin, metconazol and epoxiconazol.

In a further embodiment, the pesticide comprises an insecticide; the pesticide more preferably consists of at least one insecticide. Preferred insecticides are fipronil, allethrin, alpha-cypermethrin, beta-cyfluthrin, bifenthrin, bioallethrin, 4-chloro-2-(2-chloro-2-methylpropyl)-5-[(6-iodo-3-pyridinyl)methoxy]-3(2H)pyridazinone (CAS RN: 120955-77-3), chlorfenapyr, chlorpyrifos, cyfluthrin, cyhalothrin, cypermethrin, deltamethrin, etofenprox, fenoxycarb, flufenoxuron, hydramethylnon, metaflumizone, permethrin, pyriproxifen, silafluofen, tebufenozide and tralomethrin. Particularly preferred insecticides are fipronil, alpha-cypermethrin, bifenthrin, chlorfenapyr, cyfluthrin, cypermethrin, deltamethrin, etofenprox, hydramethylnon, metaflumizone, permethrin. Very particularly preferred insecticides are fipronil, alpha-cypermethrin, deltamethrin, chlorfenapyr, hydramethylnon and metaflumizone. An especially preferred insecticide is fipronil.

In a further embodiment, the pesticide comprises a herbicide; the pesticide preferably consists of at least one herbicide. In a further embodiment, the pesticide comprises a growth regulator; the pesticide preferably consists of at least one growth regulator.

The inventive composition typically comprises 0.5 to 50% by weight of active ingredient, preferably 1 to 30% by weight, especially 5 to 20% by weight, based on the composition. The inventive composition usually comprises 3 to 50% by weight, preferably 5 to 30% by weight, more preferably 10 to 20% by weight, of dendron (I).

The weight ratio of polyether dendron (I) to active ingredient is usually in the range from 1:50 to 100:1, preferably 1:5 to 50:1, more preferably 1:2 to 25:1. The active ingredient may be present in dissolved form or in solid particulate form. The active ingredient particles may be crystalline or amorphous. The particle size may be 1 nm to 10 μm.

The invention preferably relates to agrochemical compositions comprising the inventive mixture of the polyether dendrimer (I) and a pesticide.

Examples for composition types of the agrochemical composition are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further compositions types are defined in the "Catalogue of pesticide formulation types and international coding system", Technical Monograph No. 2, 6th Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Examples for suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are preferably water but include organic solvents, such as mineral oil fractions of medium to high boiling point, e.g. kerosene, diesel oil; oils of vegetable or animal origin; aliphatic, cyclic and aromatic hydrocarbons, e.g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharide powders, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emusifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-subsititued fatty acid amides are fatty acid glucamides or fatty acid alkanolamides.

Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable negligible or even no pesticidal activity themselves, and which improve the biological performance of the compound I on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), anorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for composition types and their preparation are:

i) Water-soluble concentrates (SL, LS)

10-60 wt-% of a mixture according to the invention and 5-15 wt-% wetting agent (e.g. alcohol alkoxylates) are dissolved in water and/or in a water-soluble solvent (e.g. alcohols) up to 100 wt-%. The active substance dissolves upon dilution with water.

ii) Dispersible concentrates (DC)

5-25 wt-% of a mixture according to the invention and 1-10 wt-% dispersant (e.g. polyvinylpyrrolidone) are dissolved in up to 100 wt-% organic solvent (e.g. cyclohexanone). Dilution with water gives a dispersion.

iii) Emulsifiable concentrates (EC)

15-70 wt-% of a mixture according to the invention and 5-10 wt-% emulsifiers (e.g. calcium dodecylbenzenesulfonate and castor oil ethoxylate) are dissolved in up to 100 wt-% water-insoluble organic solvent (e.g. aromatic hydrocarbon). Dilution with water gives an emulsion.

iv) Emulsions (EW, EO, ES)

5-40 wt-% of a mixture according to the invention and 1-10 wt-% emulsifiers (e.g. calcium dodecylbenzenesulfonate and castor oil ethoxylate) are dissolved in 20-40 wt-% water-insoluble organic solvent (e.g. aromatic hydrocarbon). This mixture is introduced into up to 100 wt-% water by means of an emulsifying machine and made into a homogeneous emulsion. Dilution with water gives an emulsion.

v) Suspensions (SC, OD, FS)

In an agitated ball mill, 20-60 wt-% of a mixture according to the invention are comminuted with addition of 2-10 wt-% dispersants and wetting agents (e.g. sodium lignosulfonate and alcohol ethoxylate), 0.1-2 wt-% thickener (e.g. xanthan gum) and up to 100 wt-% water to give a fine active substance suspension. Dilution with water gives a stable suspension of the active substance. For FS type composition up to 40 wt-% binder (e.g. polyvinylalcohol) is added.

vi) Water-dispersible granules and water-soluble granules (WG, SG)

50-80 wt-% of a mixture according to the invention are ground finely with addition of up to 100 wt-% dispersants and wetting agents (e.g. sodium lignosulfonate and alcohol ethoxylate) and prepared as water-dispersible or water-soluble granules by means of technical appliances (e.g. extrusion, spray tower, fluidized bed). Dilution with water gives a stable dispersion or solution of the active substance.

vii) Water-dispersible powders and water-soluble powders (WP, SP, WS)

50-80 wt-% of a mixture according to the invention are ground in a rotorstator mill with addition of 1-5 wt-% dispersants (e.g. sodium lignosulfonate), 1-3 wt-% wetting agents (e.g. alcohol ethoxylate) and up to 100 wt-% solid carrier, e.g. silica gel. Dilution with water gives a stable dispersion or solution of the active substance.

viii) Gel (GW, GF)

In an agitated ball mill, 5-25 wt-% of a mixture according to the invention are comminuted with addition of 3-10 wt-% dispersants (e.g. sodium lignosulfonate), 1-5 wt-% thickener (e.g. carboxymethylcellulose) and up to 100 wt-% water to give a fine suspension of the active substance. Dilution with water gives a stable suspension of the active substance.

ix) Microemulsion (ME)

5-20 wt-% of a mixture according to the invention are added to 5-30 wt-% organic solvent blend (e.g. fatty acid dimethylamide and cyclohexanone), 10-25 wt-% surfactant blend (e.g. alcohol ethoxylate and arylphenol ethoxylate), and water up to 100%. This mixture is stirred for 1 h to produce spontaneously a thermodynamically stable microemulsion.

x) Microcapsules (CS)

An oil phase comprising 5-50 wt-% of a mixture according to the invention, 0-40 wt-% water insoluble organic solvent (e.g. aromatic hydrocarbon), 2-15 wt-% acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt-% of a mixture according to the invention, 0-40 wt-% water insoluble organic solvent (e.g. aromatic hydrocarbon), and an isocyanate monomer (e.g. diphenylmethene-4,4'-diisocyanatae) are dispersed into an aqueous solution of a protective colloid (e.g. polyvinyl alcohol). The addition of a polyamine (e.g. hexamethylenediamine) results in the formation of a polyurea microcapsules. The monomers amount to 1-10 wt-%. The wt-% relate to the total CS composition.

xi) Dustable powders (DP, DS)

1-10 wt-% of a mixture according to the invention are ground finely and mixed intimately with up to 100 wt-% solid carrier, e.g. finely divided kaolin.

xii) Granules (GR, FG)

0.5-30 wt-% of a mixture according to the invention is ground finely and associated with up to 100 wt-% solid carrier (e.g. silicate). Granulation is achieved by extrusion, spray-drying or the fluidized bed.

xiii) Ultra-low volume liquids (UL)

1-50 wt-% of a mixture according to the invention are dissolved in up to 100 wt-% organic solvent, e.g. aromatic hydrocarbon.

The compositions types i) to xiii) may optionally comprise further auxiliaries, such as 0.1-1 wt-% bactericides, 5-15 wt-% anti-freezing agents, 0.1-1 wt-% anti-foaming agents, and 0.1-1 wt-% colorants.

The agrochemical compositions generally comprise between 0.01 and 95%, preferably between 0.1 and 90%, and most preferably between 0.5 and 75%, by weight of active substance. The active substances are employed in a purity of from 90% to 100%, preferably from 95% to 100% (according to NMR spectrum).

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, in particular from 0.1 to 0.75 kg per ha. In treatment of plant propagation materials such as seeds, e.g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seed) are generally required.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizer, or micronutrients, and other pesticides (e.g. herbicides, insecticides, fungicides, growth regulators, safeners) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

The invention further relates to a process for producing the inventive composition by contacting the polyether dendron and the active ingredient. The components can be contacted by commonly known methods, such as mixing, emulsifying or suspending.

The invention further relates to the use of the inventive polyether dendron in an agrochemical formulation, comprising the dendron and a pesticide, for controlling phytopathogenic fungi and/or unwanted vegetation and/or unwanted insect or mite infestation and/or for regulating the growth of plants, by allowing the composition to act on the particular pests, their surroundings or the plants to be protected from the particular pests, the soil and/or unwanted plants and/or the crop plants and/or the surroundings thereof. In addition, it is possible to use the inventive composition, especially the agrochemical formulation, to control unwanted insect or mite infestation on plants and/or to control phytopathogenic fungi and/or to control unwanted plant growth, by treating seeds of crop plants with the composition.

The invention further relates to the use of the inventive dendron for solubilizing a sparingly water-soluble active ingredient in aqueous solutions. The active ingredient preferably has a maximum solubility in water at 20° C. of 10 g/l. "Solubilization" means that more active ingredient can be brought into solution in the presence of the inventive amphiphile than in the absence thereof under otherwise identical conditions. It is preferably possible to bring at least twice the amount, more preferably at least five times the amount and especially ten times the amount into solution.

The invention further relates to a plant propagation material, specifically seeds, comprising the polyether dendron of the invention.

The examples which follow are intended to illustrate the invention without restricting it.

EXAMPLES

Methyl polyethylene glycol (MPEG1) has a mean molar mass of 350 g/mol, an OH number of 160 mg KOH/g, and is commercially available. Methyl polyethylene glycol (MPEG2) has a mean molar mass of 1000 g/mol, an OH number of 60 mg KOH/g and is commercially available. $C_{16}$-$C_{18}$-Fatty alcohol polyethylene glycol (FAPEG) has a OH number of 80 mg KOH/g and is commercially available. The Ohio numbers were measured to DIN 53 240. The acid numbers were measured to DIN EN ISO 2114. GPC was carried out with polymethyl methacrylate (PMMA) as the standard.

Comparative Example 1

Synthesis of Polar Dendron C1

A solution of 487 g of methyl polyethylene glycol MPEG1 in 600 ml of toluene was initially charged. 55.8 g of sodium hydroxide were added while stirring. The mixture was heated to 100° C., and 64.4 g of epichlorohydrin in 129 ml of toluene were added dropwise within 30 min. The mixture was then stirred at 100° C. for 2 h. Subsequently, 32.2 g of epichlorohydrin in 64 ml of toluene were metered in at 100° C. within 20 min. The mixture was then stirred at 103° C. for 2 h. Finally, 16.1 g of epichlorohydrin in 32 ml of toluene were metered in at 100° C. within 15 min, and the mixture was then stirred at 103° C. for another 20 h.

The resulting brown, turbid mixture was cooled to room temperature and filtered. Toluene was distilled off. The clear brown product C1 was characterized by GPC (Mn=2000 g/mol, Mw=2480 g/mol, in dimethylacetamide).

Example 1

Synthesis of Amphiphilic Dendron D1

A solution of 136.7 g MPEG2 and 95.7 g FAPEG in 259 ml toluene was initially charged. 22.8 g of sodium hydroxide were added while stirring. The mixture was heated to 100° C. and then 12.8 g of epichlorohydrin in 26 ml of toluene were added dropwise within 30 min. The mixture was then stirred at 100° C. for 2 h. Subsequently, 6.4 g of epichlorohydrin in 13 ml of toluene were metered in at 100° C. within 20 min. Subsequently 3.2 g of epichlorohydrine in 6 ml of toluene were metered in at 100° C. within 15 min, and the mixture was stirred at 103° C. for a further 20 h. The resulting brown, turbid mixture was cooled to room temperature and filtered. Thereafter the toluene was distilled off. The clear brown product D1 was characterized by GPC (Mn=3670 g/mol, Mw=5910 g/mol in dimethylacetamide).

Example 2

Synthesis of Amphilic Dendron D2

A solution of 240 g (1.818 mol) of 180.7 g MPEG2 and 56.5 g FAPEG in 258 ml toluene was initially charged. 20.94 of sodium hydroxide were added while stirring. The mixture was heated to 100° C. and then 12.1 of epichlorohydrin in 24 ml of toluene were added dropwise within 30 min. The mixture was then stirred at 100° C. for 2 h. Subsequently, 6.1 g of epichlorohydrin in 12 ml of toluene were metered in at 100° C. within 20 min. Then 3.0 g of epichlorohydrin in 6 ml toluene was metered in at 100° C. within 15 min, and the mixture was stirred at 103° C. for a further 20 h. The resulting dark brown, turbid mixture was cooled to room temperature and filtered. Thereafter the toluene was distilled off. The clear brown product D2 was characterized by GPC (Mn=3590 g/mol, Mw=5860 g/mol in dimethylacetamide).

Application Example 1

Increased uptake and retention of pesticide in leaves:
An aqueous suspension concentrate ("SC3") was prepared containing 300 g/l fluxapyroxad, 1,2-propylene glycol, anionic phenolsulfonic acid-urea-formaldehyde condensate surfactant, sodium salt of naphthalene sulfonate condensate, antibacterial agent and antifoaming agent, thickener. The spray mixture was applied at a rate of 200 l/ha, 12.5 g/ha pesticide and 250 g/ha polyether dendron.

The uptake of the pesticide in the leave was determined as described by Berghaus R, Nolte M, Reinold A 2010. "Optimization of agrochemical formulations by adjuvants using lab track sprayer and HPLC-MS-MS analysis". In: Baur P and Bonnet M ed. Proc. 9th Intern. Symp. on Adjuvants for Agrochemicals. ISAA 2010 Freising, Germany. Pp. 239-244: Wheat plants (Triticumaestivum variety Melon) were used. Subsequently to spraying, the plants were cultivated again in the greenhouse under ambient conditions. After 8 days samples of 10-15 treated leaves were cut off and weighed. Leaves were cut into small pieces, and washed with 50% methanol in demineralized water as washing medium for 5 min. Then, the washing medium was separated from the leaves. The leaves were washed again with washing medium for 5 min. Both washing media were combined and diluted for analysis.

Finally, the leaves were transferred to a vial containing the extraction medium (75% methanol, 20% water and 5% HCl) and homogenized using a Polytron PT 6100 dispersing unit (Kinematica, CH) for 2 min. 10 ml of the extract were centrifuged with 4000 rpm for 5 min. 2 ml of the supernatant were treated with 2 ml NaOH (0.2 mol/L) and 5 ml cyclohexane, and stirred for 30 min and centrifuged subsequently. 1 ml of the cyclohexane phase was transferred to a glass vial and dried (Liebisch N2 Evaporator, Germany). The residue was solubilized in methanol/water 50:50 and analyzed by HPLC-MS/MS. In addition, unsprayed plants were treated in the same way to see whether they are contaminated. Unsprayed leaves were spiked with standard active ingredient to determine the recovery of active ingredient during washing and extracting steps. According to the recovery rate the measured sample values were corrected. Retention (total amount of active found in and on the plant) is equal to the sum of active concentrations found during washing and extracting steps.

The results that are given in Table 1 show that the usage of invented adjuvants drastically increases the uptake of pesticide. The comparative Graft Polymers GM 903/0211 and 227 and C2 are based on a hydrogen-terminated alkoxylate instead of an alcohol alkoxylate. The data showed that this modification resulted in an increased uptake and retention of the active.

TABLE 1

|  | Uptake (mg/kg leave) |
| --- | --- |
| fluxapyroxad[a] | 0.4 |
| fluxapyroxad + C1[a] | 0.4 |
| fluxapyroxad + D1 | 0.8 |
| fluxapyroxad + D2 | 0.9 |

[a]Comparative not according to invention

Biology (Green House)

Application Example 2

Increased Efficacy—Comparative Data

An aqueous suspension concentrate ("SC1") was prepared containing 300 g/l fluxapyroxad (a fungicide, water solubility 4 mg/L at 20° C.) and common auxiliaries (such as 1,2-propylene glycol, anionic phenolsulfonic acid-urea-formaldehyde condensate surfactant, antibacterial agent, antifoaming agent, thickener).

The pesticidal activity was tested in greenhouse tests on wheat variety Monopol, which were infected with the fungi *Puccinia Recondata/Tritici*. The plants were treated with SC1 three days after the inoculation at a use rate of 25, 8.25 or 2.75 g pesticide per ha (200 I water/ha). The use rate of the adjuvants was kept constant at 250 g per ha. The percentage of the infected leaf surface areas (7 days after inoculation) was summarized in Table 2.

The data showed that compositions with the dendrons D1 and D2 according to the invention have a higher pesticidal activity compared to the control without the dendron.

TABLE 2

|  |  | % Use rate of active | |
| --- | --- | --- | --- |
|  |  | 100% | 33% |
|  |  | % infected leaf area | |
| C2[a] | Untreated | 80% | |
| C3[a] | fluxapyroxad | 79% | 80% |
| Ap. Ex. 2.1 | fluxapyroxad D1 | 7% | 31% |
| Ap. Ex. 2.2 | fluxapyroxad D2 | 12% | 45% |

[a]Comparative not according to invention

The above greenhouse tests were also made with a suspension concentrate "SC2" of the triazole fungicide 2-[4-(4-chlorophenoxy)-2-(trifluoromethyl)phenyl]-1-(1H-1,2,4-triazol-1-yl)propan-2-ol "fungicide 2" (100 g/ha) instead of fluxapyroxad. The results are summarized in Table 3:

TABLE 3

|  |  | % Use rate of active | |
| --- | --- | --- | --- |
|  |  | 100% | 33% |
|  |  | % infected leaf area | |
| C4[a] | Untreated | 89% | |
| C5[a] | fungicide 2 | 83% | 91% |
| Ap. Ex. 3 | fungicide 2 D1 | 6% | 12% |

[a]Comparative not according to invention

Application Example 3

Solubilization of Pesticides

Solubilization measurements were carried out with a highthroughput screening robot. This set up dosed 10 mg solid active and 500 μm of the respective 3 wt-% liquid polymer solution (in CIPAC water D) into wells on a micro titer plate. After the addition of stirring bars and 24 hours incubation time the samples were filtrated via polypropylene filters in order to separate dissolved active and its solid form ated. The amount of solubilized active was determined via UV/VIS spectroscopy. The solubilities of various actives were summarized in Tables 4.

TABLE 4

| Increased solubility of fluxapyroxad |  |
| --- | --- |
|  | Solubility in pmm |
| fluxapyroxad alone[a] | 10 |
| C1[a] | 19 |

TABLE 4-continued

Increased solubility of fluxapyroxad

|  | Solubility in pmm |
|---|---|
| D1 | 650 |
| D2 | 409 |

[a]Comparative not according to invention

TABLE 5

Increased solubility of fipronil

|  | Solubility in pmm |
|---|---|
| Fipronil[a] | 12 |
| C1[a] | 14 |
| D1 | 840 |

[a]Comparative not according to invention

TABLE 6

Increased solubility of the triazole fungicide 2-[4-(4-chlorophenoxy)-2-(trifluoromethyl)phenyl]-1-(1H-1,2,4-triazol-1-yl)propan-2-ol (BAS 750 F)

| BAS 750 F | Solubility in pmm |
|---|---|
| Active without polymer[a] | 15 |
| Active with D1 | 1234 |

[a]Comparative not according to invention

TABLE 7

Increased solubility of fenofibrate

| Fenofibrate | Solubility in pmm |
|---|---|
| Active without polymer[a] | 0 |
| Active with D1 | 281 |

[a]Comparative not according to invention

TABLE 8

Increased solubility of carbamazepine

| cabamazepine | Solubility in pmm |
|---|---|
| Active without polymer[a] | 181 |
| Active with D1 | 1032 |

[a]Comparative not according to invention

Application Example 4

Increased Storage Stability of Suspension Concentrate

An aqueous suspension concentrate "SC4" was prepared comprising 80 g/l fluxapyroxad, 80 g/l graft polymer (see Table 6), 25 g/l 1,2-propylene glycol, 13 g/L sodium salt of naphthalene sulfonate condensate, 1.5 g/l xanthan gum, 5 g/l anionic phenolsulfonic acid-urea-formaldehyde condensate, silicon defoamer, and antibacterials. For comparison, the aqueous suspension concentrate "SC4" was prepared without the addition of any graft polymer ("SC4 without graft polymer"). The suspension concentrates were stored for 14 days at 20° C. or at 40° C. The stability of the formulation was determined by using instrument Malvern. D90 is the value in μm that 90% (volume/volume) of the particles existing in the formulation have a size smaller this value. An increase in D 90 is an indication for the destabilization of SC formulations.

TABLE 9

Particle size D90 during storage of suspension concentrate "SC4"

|  | D (90) | | |
|---|---|---|---|
|  | 0 d | 14 d at 20° C. | 14 d at 20° C. |
| Reference formulation | 2.0 μm | 2.0 μm | 2.0 μm |
| D1 | 1.9 μm | 2.0 μm | 1.9 μm |
| D2 | 2.0 μm | 2.0 μm | 1.9 μm |
| Comparison Plurafac LF 300[a] | 2.0 μm | 7.9 | 7.8 |

[a]Comparative data Plurafac is a nonionic surfactant based on alkoxylated, predominantly unbranched falty alcohols, containing higher alkyleneoxide.

The comparative polymer resulted in a clear increase of particle size during storage.

The invention claimed is:

1. A composition, comprising
   a) a polyether dendron of formula (I),

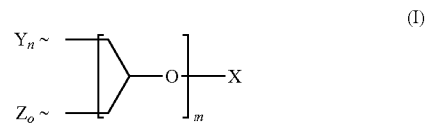

(I)

wherein the symbols and indices have the following meanings:
   each Y is independently [$R^1$—(O—$CH_2$—$CH_2$)$_p$—O—];
   each Z is independently [$R^2$—(O—$CH_2$—$CH_2$)$_q$(O—CH($CH_3$)—$CH_2$)$_r$—O—];
   each $R^1$ is independently H, $CH_3$ or $C_2$-$C_4$-alkyl;
   each $R^2$ is independently linear or branched $C_8$-$C_{22}$-alkyl;
   X is H or $C_1$-$C_4$-alkyl;
   m is 1, 2, 3, 4, 5 or 6;
   n, o are rational positive numbers >0, with the proviso that the sum of n and o is $2^m$;
   p is a natural number from 5 to 50;
   q is a natural number from 1 to 50;
   r is 0 or is a natural number from 1 to 30, with the proviso that 5≤q+r≤50, and
   ~ denotes the bonding of the respective group to the dendron scaffold; and
   b) a pesticidal active ingredient.

2. The composition of claim 1, wherein the pesticidal active ingredient has a maximum solubility in water of 10 g/l at 20° C.

3. A process for producing the composition according to claim 1, comprising the step of contacting a polyether dendron of formula (I) and a pesticidal active ingredient.

4. A method for controlling phytopathogenic fungi or undesired vegetation or insect or acarid infestations or for regulating the growth of plants, comprising the step of applying a pesticidal composition according to claim 2 to the pests or undesired plants, to plants to be protected and/or to the soil where the plants to be protected or the undesired plants grow.

5. The method of claim 4, wherein the polyether dendron has a molecular weight of 1000 to 15.000.

6. The method of claim 4, wherein group Y has a molecular weight of 300 to 2000.

7. The method of claim 4, wherein the weight ratio Y:Z is 13:1 to 1:3.

8. The method of claim 4, wherein the molar ratio of Y to Z is in the range of from 95:5 to 3:1.

9. The method of claim 4, wherein 70 to 100% of the groups Y and Z carry an end group $R^1$ or $R^2$.

10. The composition of claim 1, wherein the symbols and indices in formula (I) have the following meanings:
X is H;
each Y is the same;
each Z is independently $[R^2—(O—CH_2—CH_2)_q(O—CH(CH_3)—CH_2)_r—O—]$
$R^1$ is $CH_3$;
$R^2$ is linear or branched, $C_8$-$C_{22}$-alkyl;
m is 1, 2 or 3;
n, o are positive rational numbers with the proviso that the sum of n and o is $2^m$;
p is a natural number from 15 to 25;
q is a natural number from 5 to 25, and
r is 0 or is a natural number from 1 to 15.

11. The composition according to claim 1, wherein the polyether dendrons of formula (I) have a molecular weight of 1000 to 15.000.

12. The composition according to claim 1, wherein group Y in formula (I) has a molecular weight of 300 to 2000.

13. The composition according to claim 1, wherein the weight ratio Y:Z in formula (I) is 13:1 to 1:3.

14. The composition according to claim 1, wherein the molar ratio of Y to Z in formula (I) is in the range of from 95:5 to 3:1.

15. The composition according to claim 1, wherein 70 to 100% of the groups Y and Z in formula (I) carry an end group $R^1$ or $R^2$.

16. A process for preparing a polyether dendron of formula (I)

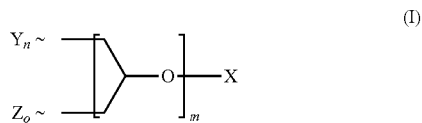

wherein the symbols and indices have the following meanings:
each Y is independently $[R^1—(O—CH_2—CH_2)_p—O—]$;
each Z is independently $[R^2—(O—CH_2—CH_2)_q(O—CH(CH_3)—CH_2)_r—O—]$;
each $R^1$ is independently H, $CH_3$ or $C_2$-$C_4$-alkyl;
each $R^2$ is independently linear or branched $C_8$-$C_{22}$-alkyl;
X is H or $C_1$-$C_4$-alkyl;
m is 1, 2, 3, 4, 5 or 6;
n, o are rational positive numbers >0, with the proviso that the sum of n and o is $2^m$;
p is a natural number from 5 to 50;
q is a natural number from 1 to 50;
r is 0 or is a natural number from 1 to 30, with the proviso that 5≤q+r≤50, and
~ denotes the bonding of the respective group to the dendron scaffold;
comprising the steps of reacting n moles (CY—H) and o moles (Z—H) with (n+o)/2 moles of glycerol or a reactive derivative thereof at a temperature of 20 to 200° C. and optionally in the presence of a catalyst and optionally repeating the step of reacting with glycerol or a reactive derivative thereof up to the number of m reactions, reacting each time half of the molar amount of glycerol or reactive glycerol derivative reacted in the last step.

* * * * *